(12) United States Patent
Jiang et al.

(10) Patent No.: US 11,944,447 B2
(45) Date of Patent: Apr. 2, 2024

(54) NEUROVASCULAR COUPLING ANALYTICAL METHOD BASED ON ELECTROENCEPHALOGRAM AND FUNCTIONAL NEAR-INFRARED SPECTROSCOPY

(71) Applicant: INSTITUTE OF AUTOMATION, CHINESE ACADEMY OF SCIENCES, Beijing (CN)

(72) Inventors: Tianzi Jiang, Beijing (CN); Xin Zhang, Beijing (CN); Nianming Zuo, Beijing (CN); Juanning Si, Beijing (CN)

(73) Assignee: INSTITUTE OF AUTOMATION, CHINESE ACADEMY OF SCIENCES, Beijing (CN)

( * ) Notice: Subject to any disclaimer, the term of this patent is extended or adjusted under 35 U.S.C. 154(b) by 1178 days.

(21) Appl. No.: 16/961,700

(22) PCT Filed: Nov. 3, 2016

(86) PCT No.: PCT/CN2016/104455
§ 371 (c)(1),
(2) Date: Jul. 13, 2020

(87) PCT Pub. No.: WO2018/081980
PCT Pub. Date: May 11, 2018

(65) Prior Publication Data
US 2021/0282694 A1    Sep. 16, 2021

(51) Int. Cl.
*A61B 5/378*    (2021.01)
*A61B 5/00*    (2006.01)
(Continued)

(52) U.S. Cl.
CPC ............ *A61B 5/378* (2021.01); *A61B 5/0075* (2013.01); *A61B 5/0261* (2013.01); *A61B 5/374* (2021.01);
(Continued)

(58) Field of Classification Search
CPC ..... A61B 5/0075; A61B 5/0261; A61B 5/374; A61B 5/291; A61B 5/31; A61B 5/369; A61B 5/372
See application file for complete search history.

(56) References Cited

U.S. PATENT DOCUMENTS

2015/0310750 A1    10/2015    Glaunsinger

FOREIGN PATENT DOCUMENTS

CN    101853070 A    *    10/2010
CN    101853070 A        10/2010
(Continued)

OTHER PUBLICATIONS

Jinyan Sun, Attention Orienting and Executive Control Respectively Studied with Event-Related Electroencephalography and a Multi-Modality Optical-Electrophysiology Method, Medicine & Public Health, 2013, pp. 1-109.

*Primary Examiner* — Tammie K Marlen
(74) *Attorney, Agent, or Firm* — Bayramoglu Law Offices LLC (57) ABSTRACT

A neurovascular coupling analytical method based on an electroencephalogram and functional near-infrared spectroscopy includes: S100: acquiring an electroencephalogram signal and a brain hemodynamic signal; S110: extracting an event-related potential signal from the electroencephalogram signal; S120: extracting a time characteristic from the event-related potential signal; S130: extracting a hemodynamic response function from the brain hemodynamic signal; S140: extracting an amplitude characteristic and time (Continued)

characteristics from the hemodynamic response function; and S150: analyzing influence of the time characteristic of the event-related potential signal on the amplitude characteristic and the time characteristics of the hemodynamic response function to obtain a coupling result. The time characteristic of the event-related potential signal is a delay. The amplitude characteristic of the hemodynamic response function is a peak amplitude, and the time characteristics of the hemodynamic response function comprises a rising delay, a peak time, and a full width at half maximum.

11 Claims, 6 Drawing Sheets (51) Int. Cl.
  *A61B 5/026* (2006.01)
  *A61B 5/374* (2021.01)
(52) U.S. Cl.
  CPC .......... *A61B 5/7207* (2013.01); *A61B 5/7282* (2013.01); *A61B 5/7285* (2013.01)

(56) References Cited

FOREIGN PATENT DOCUMENTS

| CN | 102715902 A | 10/2012 |
| CN | 105816170 A | 8/2016 |
| CN | 106580248 A | 4/2017 |

\* cited by examiner

NEUROVASCULAR COUPLING ANALYTICAL METHOD BASED ON ELECTROENCEPHALOGRAM AND FUNCTIONAL NEAR-INFRARED SPECTROSCOPY

CROSS REFERENCE TO THE RELATED APPLICATIONS

This application is the national phase entry of International Application No. PCT/CN2016/104455, filed on Nov. 3, 2016, the entire contents of which are incorporated herein by reference.

TECHNICAL FIELD

The present invention relates to the technical field of electroencephalogram and functional near-infrared spectroscopy, in particular, to a neurovascular coupling analytical method based on electroencephalogram and functional near-infrared spectroscopy.

BACKGROUND

Functional activities of the brain include neuron activities and local energy metabolism. The brain obtains a substantial amount of modal information by means of complex functional activities. The most important brain functional activities are the neuronal electrical activities and the blood oxygen metabolic changes in activation areas. The relationship between these two activities is referred to as neurovascular coupling. This complex coupling, in turn, involves a series of activities among neurons, astrocytes and capillaries. Currently, however, except that some evidence suggests neurovascular coupling may influence judgment and decision making, the relationship between blood oxygen changes and neuronal activities essentially remains a mystery in the field of neuroscience.

Neurovascular coupling is researched by using multimodal brain functional imaging fusion technology, which has been an area of growth in the field. But, such image fusing has drawbacks. Although functional magnetic resonance imaging (fMRI) has a relatively high spatial resolution and can be complemented by the electroencephalogram (EEG), which has a relatively high temporal resolution, the magnetic field signal of fMRI may be disturbed by the electrical signal of EEG resulting in significant "noise." In addition, the fMRI has strict testing requirements for the environment as well as the subject. fMRI equipment is also cumbersome and expensive, which substantially retards evolution and growth of EEG-fMRI fusion technology. Functional near-infrared spectroscopy (fNIRS), on the other hand, is an emerging technology developed in recent years. Compared with fMRI, fNIRS can detect not only changes in deoxyhemoglobin (HbR), but also changes that occur with oxyhemoglobin (HbO), and even total hemoglobin (HbT=HbO+HbR). There is almost no disturbance component between the optical signal of fNIRS and the electrical signal of EEG. In addition, due to its lower cost, ease of portability, noninvasive procedure and convenient operation, the fNIRS and the EEG equipment are preferred by many researchers. The neuronal electrical activities and the blood oxygen metabolism information in the activation areas of the brain can be synchronously captured by the combination of EEG and fNIRS, which provides optimal technical support for researching neurovascular coupling, especially in cases requiring high synchronization. The mechanism of brain neuron activity can more easily be investigated and researched as well. The relationship between the hemodynamic signal and the neuronal activity is established starting from the functional areas, and then, on this basis, the coupling differences between different brain regions are quantitatively studied. However, such a study is mainly based on the amplitude characteristics (activation intensity) of EEG and fNIRS.

In view of this, the present invention is proposed.

SUMMARY

To address deficiencies in what is known about the time characteristics of the hemodynamic response and the neuronal electrical activities in the conventional neurovascular coupling analysis, the present invention provides a neurovascular coupling analytical method based on an electroencephalogram and functional near-infrared spectroscopy.

In order to achieve the above purpose, the following technical solution is provided.

A neurovascular coupling analytical method based on electroencephalogram and functional near-infrared spectroscopy, includes:
  acquiring an electroencephalogram signal and a brain hemodynamic signal;
  extracting an event-related potential signal from the electroencephalogram signal;
  extracting a time characteristic from the event-related potential signal;
  extracting a hemodynamic response function from the brain hemodynamic signal;
  extracting an amplitude characteristic and time characteristics from the hemodynamic response function;
  analyzing an influence of the time characteristic of the event-related potential signal on the amplitude characteristic and the time characteristics of the hemodynamic response function to obtain a coupling result.

Further, the step of acquiring the electroencephalogram signal and the brain hemodynamic signal specifically includes:
  synchronously acquiring the electroencephalogram signal and the brain hemodynamic signal by a photoelectric synchronous brain activity detection system.

Further, the step of extracting the event-related potential signal from the electroencephalogram signal specifically includes:
  performing filtering, removal of electro-ocular disturbance components, detrending, data segmentation, artifact rejection and block average on the electroencephalogram signal to extract the event-related potential signal.

Further, the step of extracting the event-related potential signal from the electroencephalogram signal further includes: down-sampling.

Further, the step of extracting the time characteristic from the event-related potential signal specifically includes:
  extract the time characteristic of the event-related potential signal by a pattern reversal visual stimulation method.

Further, the time characteristic is a delay.

Further, the step of extracting the hemodynamic response function from the brain hemodynamic signal specifically includes:
  performing concentration calculation, filtering, data segmentation, artifact rejection and block average on the brain hemodynamic signal to extract the hemodynamic response function.

Further, the amplitude characteristic of the hemodynamic response function is a peak amplitude; the time characteristics of the hemodynamic response function includes a rising delay, a peak time, and a full width at half maximum.

Further, the step of analyzing the influence of the time characteristic of the event-related potential signal on the amplitude characteristic and the time characteristics of the hemodynamic response function to obtain the coupling result, specifically includes:

analyzing a relationship between the time characteristic of a single component of the event-related potential signal and the peak amplitude of the hemodynamic response function to obtain a coupling relationship; and analyzing a relationship between the time characteristic of the single component of the event-related potential signal and the rising delay, the peak time and the full width at half maximum of the hemodynamic response function, respectively, to obtain a coupling relationship.

The present invention provides a neurovascular coupling analytical method based on electroencephalogram and functional near-infrared spectroscopy. In the present invention, the electroencephalogram signal and the brain hemodynamic signal are acquired synchronously; event-related potential signal is extracted from the electroencephalogram signal; time characteristic is extracted from the event-related potential signal; hemodynamic response function is extracted from the brain hemodynamic signal; amplitude characteristic and time characteristics are extracted from the hemodynamic response function; influence of the time characteristic of the event-related potential on the amplitude characteristic and the time characteristics of the hemodynamic response function are analyzed, and therefore, the coupling result is obtained. The embodiment of the present invention discloses the relationship between the neuronal electrical activities and the hemodynamic response from the aspect of the time characteristics by means of using the influence of the time characteristic of the event-related potential signal on the amplitude characteristic and the time characteristics of the hemodynamic response function, which overcomes the limitation of the traditional analysis of the relationship only based on the amplitude. Moreover, the neuronal electrical activities and the blood oxygen metabolic changes in the activated brain regions are synchronously acquired to assist to analyze the brain functional activities, which can be applied in the clinical research of many major neuropsychiatric diseases, such as epilepsy, infantile autism and other special groups.

DETAILED DESCRIPTION OF THE EMBODIMENTS

A preferred embodiment of the present invention will be described hereinafter with reference to the drawings. It should be understood by those skilled in the art that those embodiments are only used to explain the technical principles of the present invention and are not intended to limit the scope of protection of the present invention.

The basic idea of the embodiment of the present invention is as follows. By means of the photoelectric synchronous brain activity detection system, the neuronal electrical activities and the blood oxygen metabolic changes in the same brain area are acquired synchronously by electroencephalogram technology and functional near-infrared technology, respectively. Based on the two modal data, i.e. light and electricity, the neurovascular coupling of the dual-modal fusion of electroencephalogram and brain blood oxygen is analyzed from the perspective of the time characteristics.

The relationship between the neuronal electrical activities and the hemodynamic response, i.e. the neurovascular coupling relationship, is described from the perspective of the time characteristics.

Figure 1:
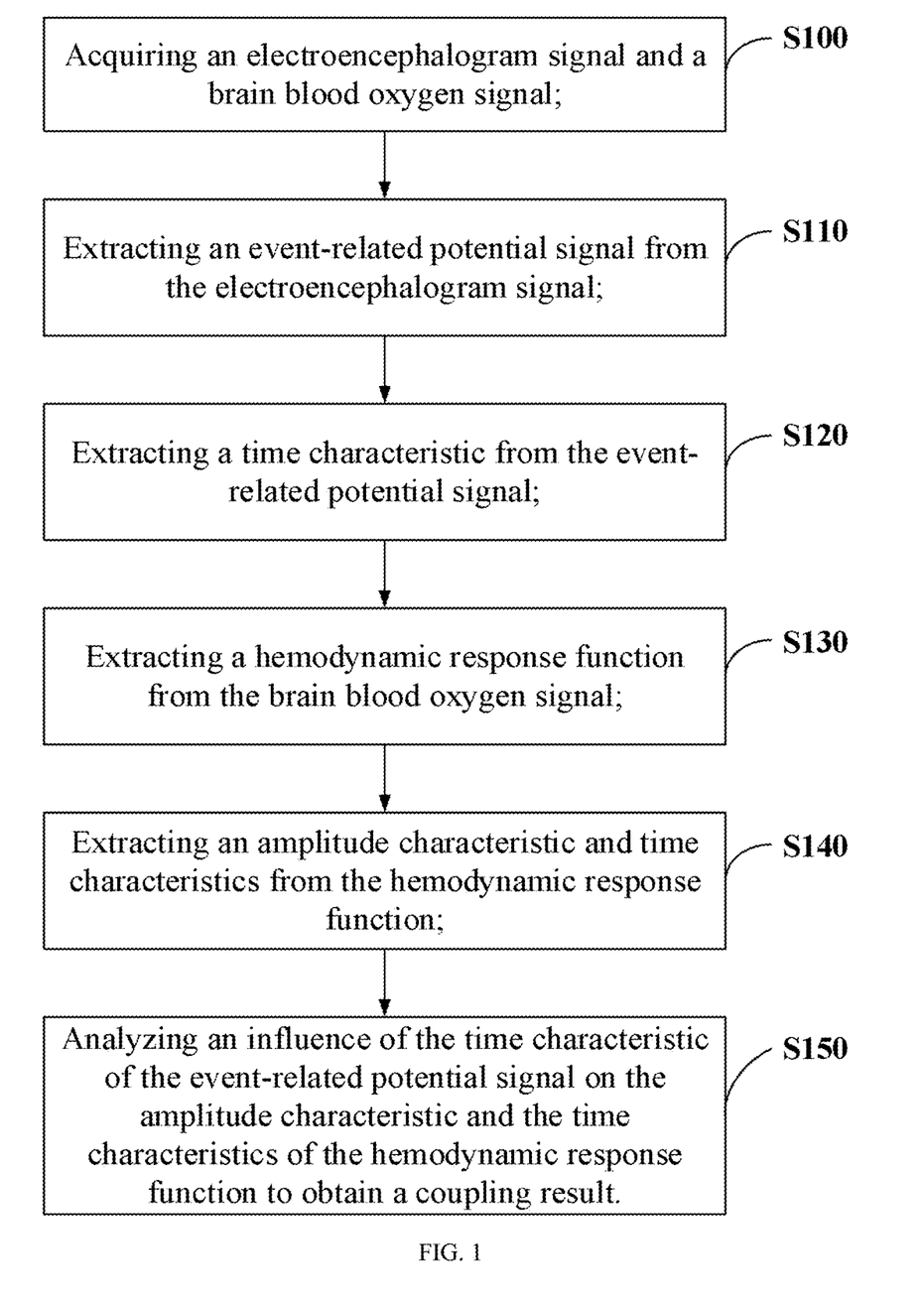
FIG. 1 is a flow diagram of a neurovascular coupling analytical method based on electroencephalogram and functional near-infrared spectroscopy according to an embodiment of the present invention.

As shown in FIG. 1, an embodiment of the present invention provides a neurovascular coupling analytical method based on electroencephalogram and functional near-infrared spectroscopy, including the following steps.

S100: the electroencephalogram signal and the brain hemodynamic signal are acquired.

In order to ensure the signal synchronization, the electroencephalogram signal and the brain hemodynamic signal can be acquired at the same time in this step.

In the practical application, the photoelectric synchronous brain activity detection system can be adopted to synchronously acquire the electroencephalogram signal and the brain hemodynamic signal. The multi-channel synchronous acquisition of the electroencephalogram signal and the brain hemodynamic signal is performed on the subject through the photoelectric synchronous brain activity detection system. According to the configured acquisition positions, the electroencephalogram signal and the brain hemodynamic signal of all configured channels are acquired at the same time, which can ensure the signal synchronization between configured channels.

S110: the event-related potential signal is extracted from the electroencephalogram signal.

Specifically, in this step, the acquired electroencephalogram (EEG) signal can be processed by filtering, down-sampling, removing the components of electro-ocular disturbance, detrending, data segmentation, artifact rejection and block average to extract the event-related potential signal (ERP).

Preferably, the filtering can be band-pass filtering to extract the band of interest of the electroencephalogram signal, such as 1-100 Hz, or to extract the rhythmic component of the electroencephalogram signal, such as delta rhythm (<4 Hz), theta rhythm (4-7 Hz), alpha rhythm (8-15 Hz), beta rhythm (16-30 Hz), etc.

It should be noted that in the above step, since too high sampling frequency and too long acquisition time will lead to massive data, the process of down-sampling can be conducted according to actual needs.

The above-mentioned process of removing the components of the electro-ocular disturbance can refer to removing the components related to the electro-ocular signal based on the independent component analysis (ICA) (for example, removing the components disturbed by the electro-ocular signal).

The above-mentioned process of detrending can refer to eliminating the drift considering the direct current (DC) component of the signal by detrending.

The above-mentioned process of data segmentation can refer to segmenting the data into a plurality of data segments according to the time mark of the event.

The above-mentioned process of artifact rejection can refer to removing the data segment with a large motion artifact. Preferably, the following method can be adopted for removing the artifact: a certain threshold value is set, when the amplitude of the electroencephalogram signal exceeds the threshold value, the corresponding data segment will not be recorded in the subsequent process of block average.

The above-mentioned process of block average can refer to synthesizing the processed data segments, and block average to extract the event-related potential (ERP) signal.

S120: the time characteristic is extracted from the event-related potential signal.

Visual evoked potential (VEP) is an electrical activity produced by the occipital lobe of the cerebral cortex subjected to visual stimulation, which represents the potential change caused by the stimulation that is received by the retina and transmitted to the occipital lobe of the cerebral cortex through visual pathway. The VEP has two very important parameters: amplitude characteristic (amplitude) and delay characteristic (delay, which is regarded as time characteristic). The amplitude represents the amount of information reaching the visual cortex, and the delay represents the time from a moment of the visual stimulation received by the retina to a moment of the visual stimulation transmitted to the visual cortex. VEP can provide important clinical diagnosis information of the functional integrity of the visual system. In 1970, VEP was used to test the vision of infants and children, and thereafter, VEP has been increasingly used by clinicians and researchers. In this way, by measuring the amplitude and the delay of various components caused by visual stimulation, the integrity of the visual pathway is evaluated, and visual related diseases are diagnosed.

With the evolution of brain science, the research of neurovascular coupling by using multimodal brain functional imaging fusion technology has gained attention in recent years. Because of the unique structural and functional characteristics of visual cortex, VEP is frequently used to study the neurovascular coupling relationship of visual cortex. Such research is mainly based on the VEP amplitude, focusing on the relationship between the VEP amplitude and the hemodynamic response. However, little is known of the influence VEP time characteristic (latency time) has on the hemodynamic response. There are no published studies with respect to VEP delay as a parameter or regarding the relationship between the VEP delay and the hemodynamic response. Many studies on the visual stimulation based on different contrasts have found that VEP amplitude mainly reflects the type and configuration information of the stimulation, while VEP delay mainly reflects the contrast and brightness information of the stimulation. Some visual information is encoded in the VEP delay, that is to say, the contrast and brightness of visual stimulation are mainly encoded in delay information, while the type and configuration of the stimulation are mainly encoded in amplitude information. Time code (time characteristic) is mainly used to distinguish small contrast differences, while neuronal discharging rate (amplitude characteristic) is mainly used to distinguish the overall difference. Hence, the VEP delay and the VEP amplitude are equally important. In the neurovascular coupling analysis, the VEP delay is an important parameter.

The amplitude characteristic and the time characteristic of the event-evoked potential signal can be acquired by many ways. For example, in the present step, the amplitude characteristic and the time characteristic of the event-evoked potential signal can be acquired by using the pattern reversal visual stimulation method.

Figure 2:
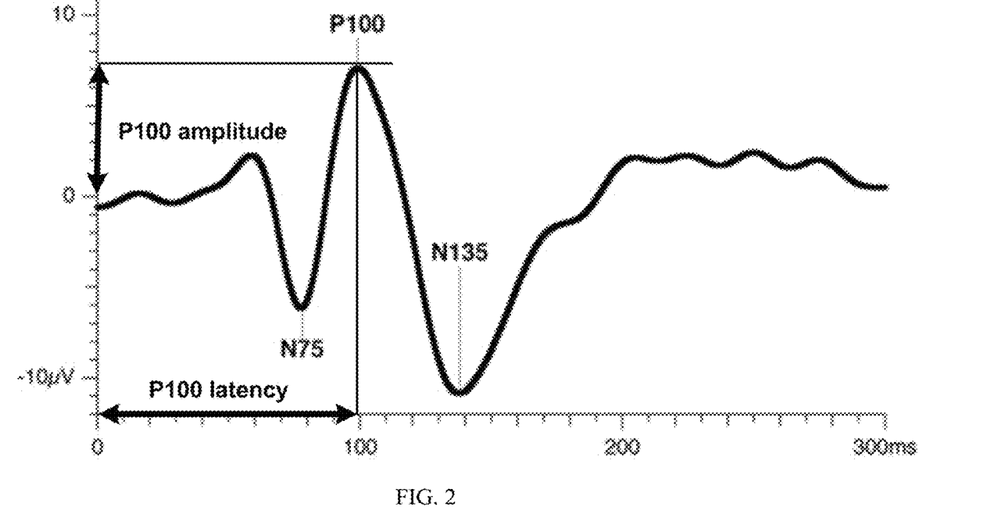
FIG. 2 is a schematic diagram of a visual evoked potential (VEP) corresponding to a visual pattern reversal experiment according to an embodiment of the present invention.

FIG. 2 is a schematic diagram of a visual evoked potential corresponding to a visual pattern reversal experiment, wherein, the X-axis represents time (latency) and the Y-axis represents amplitude. FIG. 2 shows the first negative peak (N75) at about 75 ms, the first positive peak (P100) at about 100 ms, and the second negative peak (N135) at about 135 ms.

In the embodiment of the present invention, for example, the amplitude characteristic and the time characteristic can be extracted according to the peak and the trough of VEP, wherein each extreme value represents a component. As shown in FIG. 2, for the second component P100 that appears at 100 ms, the second component P100 includes two main characteristics simultaneously, that is, the amplitude characteristic is about 7.5 uV, and the time characteristic (e.g., delay) is 100 ms.

S130: the hemodynamic response function is extracted from the brain hemodynamic signal.

Specifically, in a preferred embodiment, in the present step, the brain hemodynamic signal can be processed by concentration calculation, filtering, data segmentation, artifact rejection, and block average, to extract the hemodynamic response function (HRF).

The above-mentioned process of concentration calculation can refer to converting the original voltage signal to the concentration change signal of HbO, HbR and HbT according to the modified Beer-Lambert law (MBLL).

The above-mentioned process of filtering can refer to eliminating the noise signal that is not related to the task, such as high-frequency instrumental noise and low-frequency physiological noise (such as breath, heartbeat, Mayer wave, etc.).

The above-mentioned process of data segmentation can refer to segmenting the data into a plurality of data segments according to the time mark of the event.

The above-mentioned process of artifact rejection refers to eliminating the data segment with a large motion artifact.

The above-mentioned process of block average refers to synthesizing the processed data segments to obtain the hemodynamic response function (HRF).

S140: the amplitude characteristic and the time characteristics of the hemodynamic response function are extracted.

Figure 3:
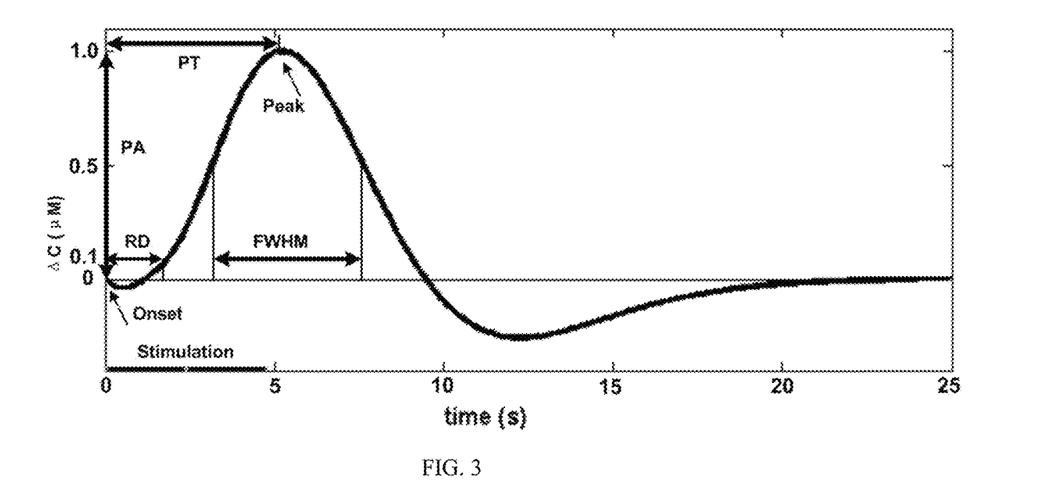
FIG. 3 is a schematic diagram of a hemodynamic response function (HRF) according to an embodiment of the present invention.

FIG. 3 is a schematic diagram of a hemodynamic response function. It mainly includes a rising segment, a plateau segment and a falling segment; wherein, the change of blood oxygen concentration is represented by AC, the peak amplitude is represented by PA, the peak time is represented by PT, the rising delay is represented by RD, the full width at half maximum is represented by FWHM, the peak of hemodynamic response is represented by Peak, the onset of the stimulation is represented by Onset, the time length of the stimulation is represented by Stimulation.

The amplitude characteristic of the hemodynamic response function includes a peak amplitude (PA).

The time characteristics of the hemodynamic response function include:
(a) rising delay (RD), that is, the time from the onset of the stimulation to 10% of the maximum value of the rising segment of the response curve;
(b) peak time (PT), that is, the time from the onset of the stimulation to the maximum value of the response curve;
(c) FWHM (full width at half maximum), i.e. the duration from 50% of the maximum value in the rising segment to 50% of the maximum value in the falling segment of the response curve.

S150: the influence of the time characteristic of the event-related potential signal on the amplitude characteristic and the time characteristics of the hemodynamic response function is analyzed to obtain the coupling result.

In the present step, the influence of the time characteristic (i.e. latency time) of components of the event-related potential on the hemodynamic response (e.g. amplitude, rising delay, peak time and the full width at half maximum of the hemodynamic response) is analyzed, and the inherent relationship between the two modal signals is extracted.

Specifically, in a preferred embodiment, the step S150 may include:

S151: the relationship between the time characteristic (latency time) of a single component of the event-related potential signal and the peak amplitude (PA) of HbO/HbR of the hemodynamic response is analyzed to obtain the coupling relationship.

S152: the relationship between the time characteristic (latency time) of the single component of the event-related potential signal and the rising delay (RD), the peak time (PT) and the full width at half maximum (FWHM) of HbO/HbR of the hemodynamic response are analyzed, respectively, to obtain the coupling relationship.

The embodiment of the present invention focuses on the influence of the time characteristic (latency time) of the electroencephalogram evoked potential signal on the parameters such as the peak amplitude, peak time, rising delay and full width at half maximum of the hemodynamic response in the activated brain, and discloses the relationship between the neuronal electrical activities and the hemodynamic response from the aspect of the time characteristics.

The present invention is described in detail hereinafter with reference to a preferred embodiment in combination with FIGS. 4a-7.

Since the visual cortex has unique structural and functional features, the present invention is described in detail as follows, taking a classic visual black-and-white checkerboard reversal experiment as an example.

Figure 4A:
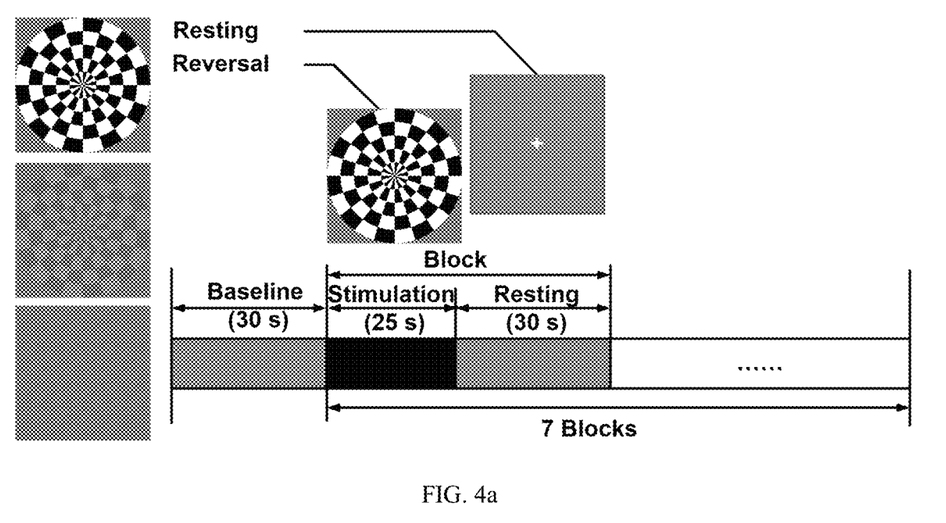
FIG. 4a is a schematic diagram of the experimental paradigm (chessboard reversal stimulation time of 25 s and resting time of 30 s) in the visual black-and-white checkerboard reversal experiment according to an embodiment of the present invention.
Figure 4B:
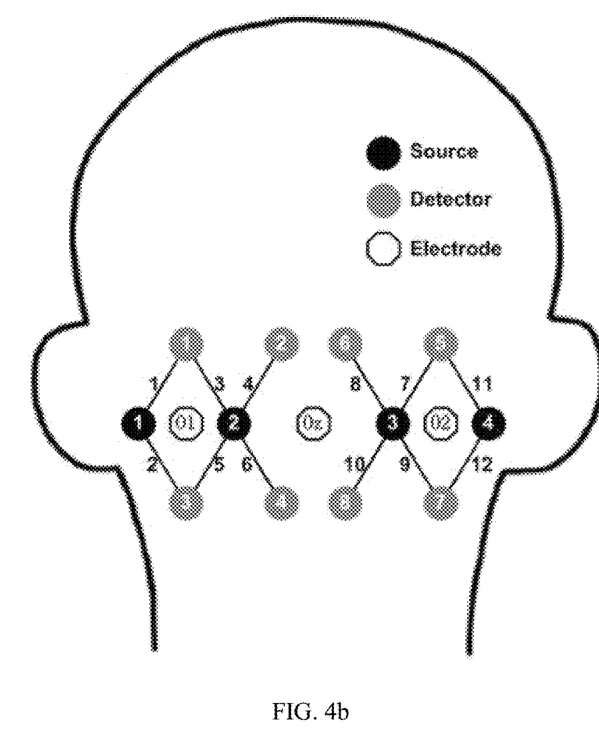
FIG. 4b is a schematic diagram of the arrangement of a near-infrared light source and an electroencephalogram electrode in the visual black-and-white checkerboard reversal experiment according to the embodiment of the present invention.

In the visual black-and-white checkerboard reversal experiment based on different contrasts according to the preferred embodiment, the time characteristic (latency time) of a single component of the event-related potential signal and the peak amplitude (PA) of the HbO of hemodynamic response are adopted to illustrate the coupling analysis process. The paradigm of the visual black-and-white checkerboard reversal experiment includes 7 blocks. Each block contains the checkerboard reversal stimulation time of 25 s and the resting time of 30 s. The visual stimulation with three contrasts (1%, 10%, and 100%) appears randomly. As shown in FIG. 4a, the baseline is represented by Baseline, the stimulation time is represented by Stimulation, the resting time is represented by Resting, and the black-and-white checkerboard reversal is represented by Reversal. The near-infrared light sources and the electroencephalogram electrodes are arranged as shown in FIG. 4b, wherein, the near-infrared light source and detector are represented by black and gray circles, respectively, the electroencephalogram electrodes are represented by hexagons, and the optical channels are represented by black solid lines.

S1: the EGG signal and the fNIRS signal are acquired.

Figure 5A:
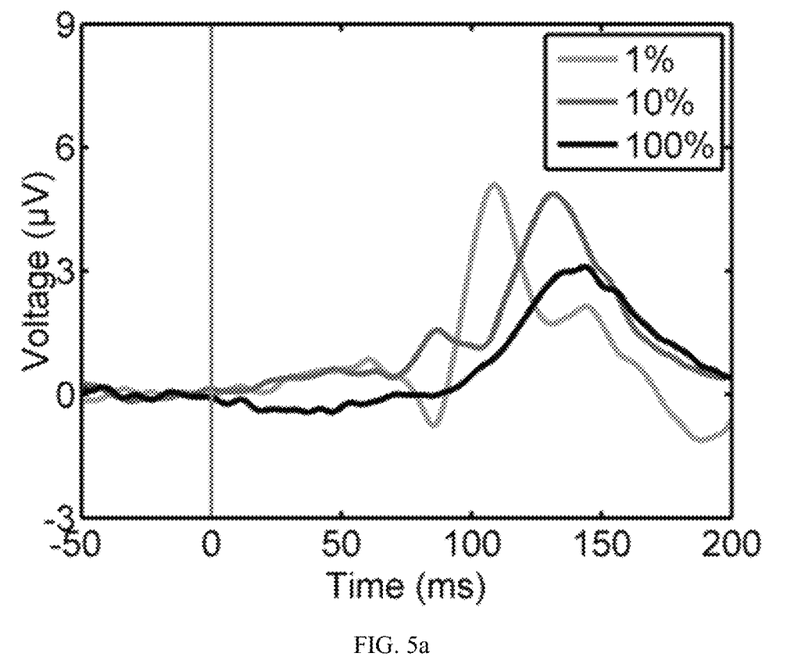
FIG. 5a is a schematic diagram of a VEP waveform under different contrasts according to the embodiment of the present invention.

S2: the acquired EGG signal is processed by filtering, down-sampling, removing the components of the electro-ocular disturbance, detrending, data segmentation, artifact rejection and block average, to obtain the VEP under different contrasts, as shown in FIG. 5a. In FIG. 5a, the X-axis represents the time, and the Y-axis represents the voltage.

S3: the delay characteristic is extracted based on the VEP signal.

Figure 5B:
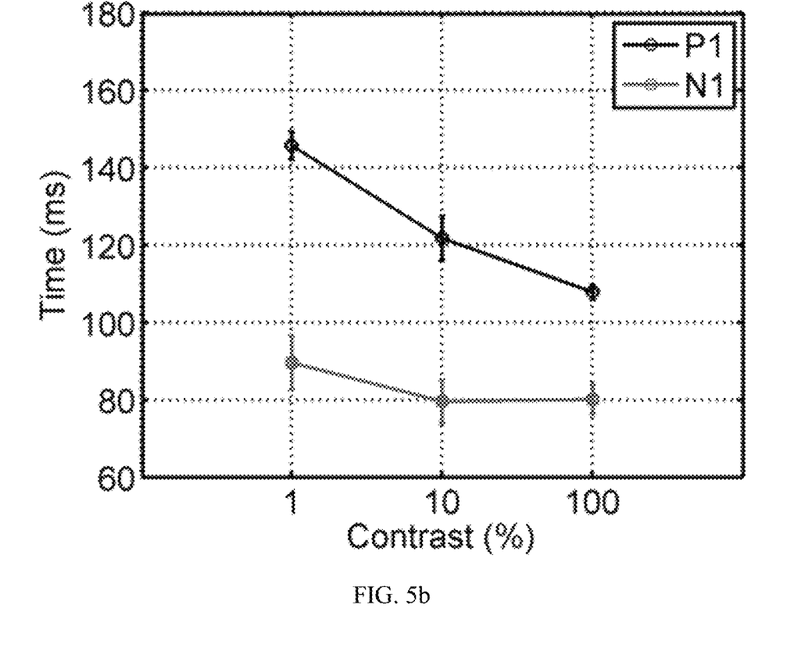
FIG. 5b is a schematic diagram of the relationship between a VEP delay and contrast according to the embodiment of the present invention.

FIG. 5b is a schematic diagram showing the relationship between the VEP delay and the contrast, wherein P1 is the first positive peak in the VEP waveform and N1 is the first negative peak in VEP waveform.

Figure 6A:
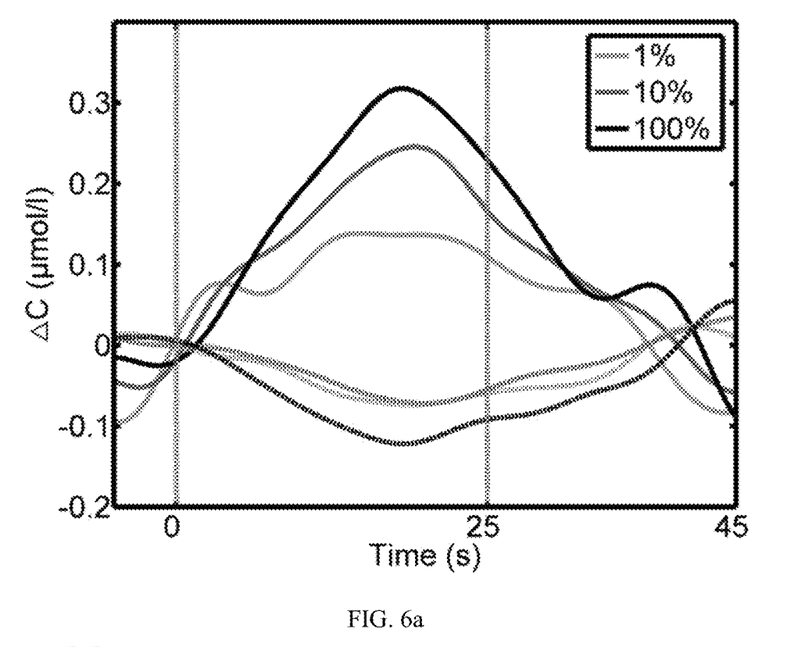
FIG. 6a is a schematic diagram of an HRF waveform under different contrasts according to the embodiment of the present invention.

S4: the acquired fNIRS signal is preprocessed by concentration calculation, filtering, data segmentation, artifact rejection and block average, to obtain the hemodynamic response function (HRF) under different contrasts, as shown in FIG. 6a, wherein the change of blood oxygen concentration is indicated by AC, the change of oxyhemoglobin (HbO) concentration is indicated by solid lines, and the change of deoxyhemoglobin (HbR) concentration is indicated by dashed lines.

S5: the amplitude characteristic is extracted according to the hemodynamic response function.

Figure 6B:
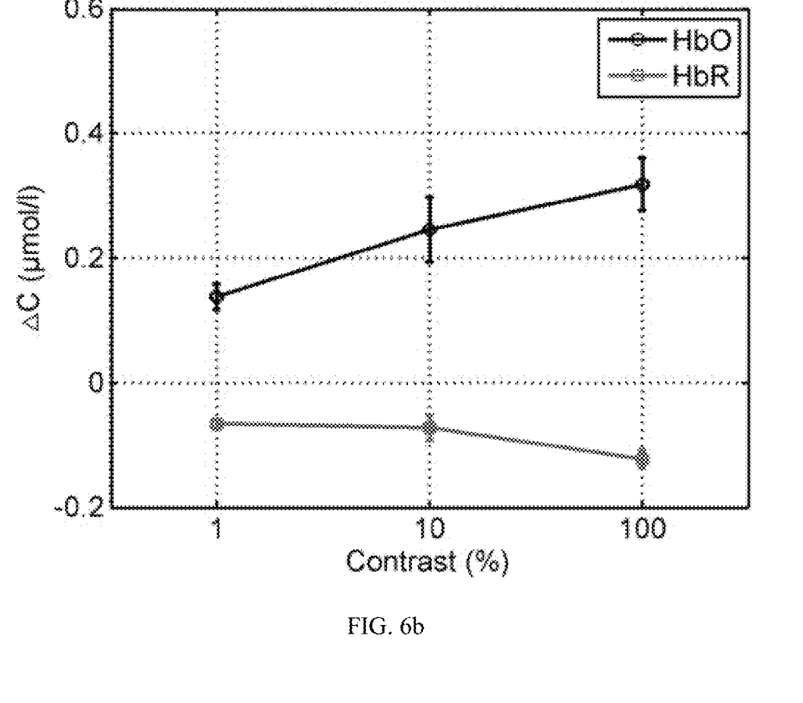
FIG. 6b is a schematic diagram of the relationship between HRF activation intensity and contrast according to the embodiment of the present invention.

FIG. 6b is a schematic diagram showing the relationship between the activation intensity of the HRF and the contrast.

Figure 7:
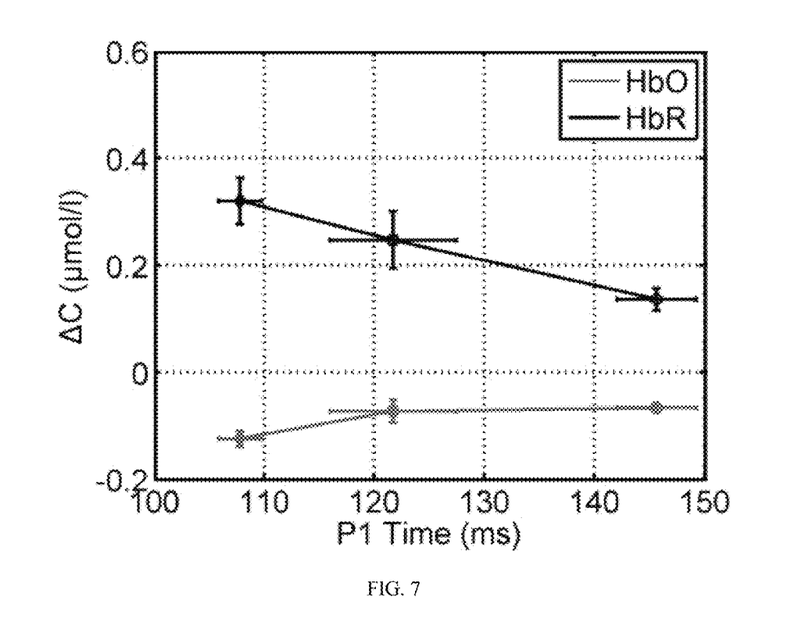
FIG. 7 is a schematic diagram of a neurovascular coupling relationship according to an embodiment of the present invention.

S6: the characteristics extracted from the EGG signal and the fNIRS signal are jointly analyzed to obtain the coupling relationship.

FIG. 7 is a schematic diagram showing the coupling relationship curve obtained from the joint analysis of the characteristics extracted from the EGG signal and the fNIRS signal, wherein, ΔC represents the change of blood oxygen concentration.

Figure 8:
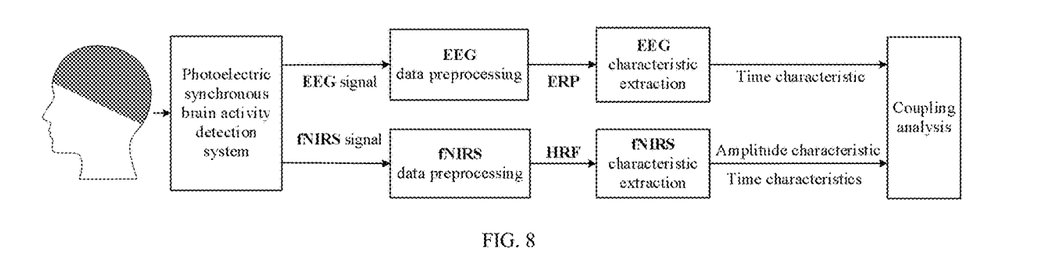
FIG. 8 is a flow diagram of a neurovascular coupling analysis method based on electroencephalogram and functional near-infrared spectroscopy according to another embodiment of the present invention.

It should be noted that although the steps in the above embodiment are described in the above order, it is understood by those skilled in the art that in order to achieve the effect of the present embodiment, it is not necessary to execute different steps in the above order, and the steps can be executed simultaneously (in parallel) or in reverse order. These simple changes shall fall within the scope of protection of the present invention. For example, as shown in FIG.

8, the processing flow of the electroencephalogram signal and the processing flow of hemodynamic response can be in parallel, and there is no sequence or cascade relationship between them. In FIG. 8, the photoelectric synchronous brain activity detection system synchronously acquires the EEG signal and the fNIRS. After that, the data preprocessing of the EEG signal and the fNIRS can be performed at the same time, and the characteristics of the EEG signal and the fNIRS can be extracted at the same time. Finally, the coupling analysis is performed.

According to the above embodiments, for strong stimulation (such as the stimulation with 100% contrast in the embodiment), neurons can usually give a relatively great response in a relatively short time. In other words, with the increase of contrast (with the enhancement of stimulation), the intensity of neuronal activity increases and the required synchronization time decreases. In addition, the neuronal activity needs to consume a lot of energy that is mainly supplied and delivered through the blood flow, and therefore, for the strong stimulation, neurons require more energy to synchronously generate action potentials in a very short time, thus causing a larger activation amplitude of the hemodynamic response. The mechanism in the present invention based on time characteristics (the amplitude of hemodynamic response increases as the delay time of the neuronal activity decreases) does not conflict with the traditional mechanism based on activation intensity (the amplitude of hemodynamic response increases as the intensity of neuronal activity increases). Furthermore, the mechanism based on the time characteristics provides more comprehensive and in-depth information for studying and illuminating the relationship between the neuronal electrical activities and the hemodynamic response.

Hereto, the technical solution of the present invention has been described with reference to the preferred embodiments in combination with the drawings. However, it is easy for those skilled in the art to understand that the scope of protection of the present invention is obviously not limited to these specific embodiments. Without departing from the principle of the present invention, those skilled in the art can make equivalent changes or substitutions to relevant technical features, and the technical solutions after these changes or substitutions shall fall within the scope of protection of the present invention.

What is claimed is:

1. A neurovascular coupling analytical method based on electroencephalogram and functional near-infrared spectroscopy, comprising:
   acquiring an electroencephalogram signal and a brain hemodynamic signal;
   extracting an event-related potential signal from the electroencephalogram signal;
   extracting a first time characteristic from the event-related potential signal;
   extracting a hemodynamic response function from the brain hemodynamic signal;
   extracting an amplitude characteristic and second time characteristics from the hemodynamic response function wherein the amplitude characteristic of the hemodynamic response function is a peak amplitude, and the second time characteristics of the hemodynamic response function comprises a rising delay, a peak time, and a full width at half maximum;
   analyzing a relationship between the first time characteristic of a single component of the event-related potential signal and the peak amplitude of the hemodynamic response function to obtain a first coupling relationship; and
   analyzing a relationship between the first time characteristic of the single component of the event-related potential signal and the rising delay, the peak time and the full width at half maximum of the hemodynamic response function, respectively, to obtain a second coupling relationship.

2. The neurovascular coupling analytical method according to claim 1, wherein, the step of acquiring the electroencephalogram signal and the brain hemodynamic signal specifically comprises:
   synchronously acquiring the electroencephalogram signal and the brain hemodynamic signal by a photoelectric synchronous brain activity detection system.

3. The neurovascular coupling analytical method according to claim 2, wherein the first time characteristic of the event-related potential signal is a delay.

4. The neurovascular coupling analytical method according to claim 1, wherein, the step of extracting the event-related potential signal from the electroencephalogram signal specifically comprises:
   performing filtering, removing components of electroocular disturbance, detrending, data segmentation, artifact rejection and block average on the electroencephalogram signal to extract the event-related potential signal.

5. The neurovascular coupling analytical method according to claim 4, wherein, the step of extracting the event-related potential signal from the electroencephalogram signal further comprises: down-sampling.

6. The neurovascular coupling analytical method according to claim 5, wherein the first time characteristic of the event-related potential signal is a delay.

7. The neurovascular coupling analytical method according to claim 4, wherein the first time characteristic of the event-related potential signal is a delay.

8. The neurovascular coupling analytical method according to claim 1, wherein, the step of extracting the first time characteristic from the event-related potential signal specifically comprises:
   extracting the first time characteristic of the event-related potential signal by a pattern reversal visual stimulation method.

9. The neurovascular coupling analytical method according to claim 8, wherein the first time characteristic of the event-related potential signal is a delay.

10. The neurovascular coupling analytical method according to claim 1, wherein the first time characteristic of the event-related potential signal is a delay.

11. The neurovascular coupling analytical method according to claim 1, wherein, the step of extracting the hemodynamic response function from the brain hemodynamic signal specifically comprises:
   performing concentration calculation, filtering, data segmentation, artifact rejection and block average on the brain hemodynamic signal to extract the hemodynamic response function.

* * * * *